(12) United States Patent
Alabdulwahhab et al.

(10) Patent No.: US 9,345,833 B1
(45) Date of Patent: May 24, 2016

(54) DENTAL INSTRUMENT

(71) Applicant: KING SAUD UNIVERSITY, Riyadh (SA)

(72) Inventors: Bander Mohammed Alabdulwahhab, Riyadh (SA); Lamia Abdulaziz Binhuwaishel, Riyadh (SA); Ghadah Awadh Al-Anazi, Riyadh (SA); Asma Ibrahim Al-Qubaisi, Riyadh (SA); Essam Ali Al-Bahkali, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/620,127

(22) Filed: Feb. 11, 2015

(51) Int. Cl.
| | |
|---|---|
| *A61M 5/24* | (2006.01) |
| *A61M 5/32* | (2006.01) |
| *A61M 5/315* | (2006.01) |
| *A61M 19/00* | (2006.01) |

(52) U.S. Cl.
CPC ......... *A61M 5/2466* (2013.01); *A61M 5/31566* (2013.01); *A61M 5/3202* (2013.01); *A61M 19/00* (2013.01); *A61M 2005/247* (2013.01); *A61M 2210/0631* (2013.01)

(58) Field of Classification Search
CPC .......... A61M 5/2466; A61M 5/31566; A61M 5/3202; A61M 19/00; A61M 2210/0631; A61M 2005/247; A61M 35/003; A61M 5/422; A61M 11/007; A61M 11/06; A61M 5/42; A61M 2005/3267; A61M 2005/1426; A61M 5/3243; A61M 5/23

See application file for complete search history.

(56) References Cited

U.S. PATENT DOCUMENTS

| | | | | |
|---|---|---|---|---|
| 2,821,981 | A | * | 2/1958 | Kish et al. ........................ 604/71 |
| 3,605,742 | A | * | 9/1971 | Tibbs ............................. 604/112 |
| 5,584,818 | A | * | 12/1996 | Morrison ....................... 604/197 |
| 6,079,868 | A | | 6/2000 | Rydell |
| 8,100,865 | B2 | | 1/2012 | Spofforth |
| 8,500,678 | B1 | * | 8/2013 | Leibovici ........................ 604/69 |
| 8,535,276 | B2 | | 9/2013 | Salzman |
| 2008/0171969 | A1 | | 7/2008 | Byrne et al. |
| 2010/0211010 | A1 | | 8/2010 | Wycoki |
| 2010/0286791 | A1 | | 11/2010 | Goldsmith |
| 2012/0197222 | A1 | | 8/2012 | Donnay et al. |

* cited by examiner

*Primary Examiner* — Nathan R Price
*Assistant Examiner* — Weng Lee
(74) *Attorney, Agent, or Firm* — Richard C. Litman

(57) ABSTRACT

The dental instrument includes a syringe and a topical anesthetic dispenser that is slidably attached to the syringe. The topical anesthetic dispenser can include a dispenser plunger, a dispenser barrel that slidably engages the dispenser plunger, a dispenser tube, and a needle cover affixed to the dispenser tube. The syringe can include a syringe plunger, a syringe barrel that slidably engages the syringe plunger, and a hollow needle having a beveled front end and a rear end extending toward the syringe barrel. A first carpule containing topical anesthetic can be loaded in the dispenser barrel. A second carpule containing injectable anesthetic solution can be loaded in the syringe barrel.

8 Claims, 3 Drawing Sheets

DENTAL INSTRUMENT

BACKGROUND OF THE INVENTION

1. Field of the Invention

The present invention relates to a dental device, and particularly to a dental instrument including a dental syringe and a topical anesthetic dispenser.

2. Description of the Related Art

While anesthetic solutions are typically administered to minimize pain associated with a particular dental procedure, the process of injecting the anesthetic solution itself can be very painful. Various topical agents are employed to minimize the pain that would otherwise be experienced by the injection. Topical anesthetics, for example, in the form of gels (Benzocaine), sprays (Tetracaine), patches (Lidocaine, EMLA made of lidocaine and prilocaine), and creams (EMLA) can be used to provide relief from pain associated with the injection.

Traditionally, administration of the topical anesthetic and the injectable anesthetic has been a cumbersome process, requiring the use of separate instruments and preparation measures. The prescribed protocol for sterilizing the target zone, preparing the instruments, and applying the topical anesthetic can significantly increase the overall time a caregiver must spend with each patient prior to administering the anesthetic injection. Oftentimes, multiple caregivers can be required to topically apply the anesthetic and administer the injection. In addition, a caregiver using a needle for injecting the anesthetic solution must take extra care to avoid accidental needle pricks and infectious needle stick injuries. The risk of an accidental needle stick injury is particularly high when a caregiver attempts to recap the needle after injection.

Thus, a dental instrument solving the aforementioned problems is desired.

SUMMARY OF THE INVENTION

The dental instrument includes a syringe and a topical anesthetic dispenser that is slidably attached to the syringe. The topical anesthetic dispenser can include a dispenser plunger, a dispenser barrel that slidably engages the dispenser plunger, a dispenser tube, and a needle cover affixed to the dispenser tube. The syringe can include a syringe plunger, a syringe barrel that slidably engages the syringe plunger, and a hollow needle having a beveled front end and a rear end extending toward the syringe barrel. A first carpule containing topical anesthetic can be loaded in the dispenser barrel. A second carpule containing injectable anesthetic solution can be loaded in the syringe barrel.

When not in use, the needle cover can be positioned to extend circumferentially around the needle and protrude beyond the needle tip to avoid accidental needle pricks. In use, a user can push the dispenser plunger in the direction of a target area to thereby slide the barrel dispenser barrel forward and/or eject the topical anesthetic from the first carpule through the dispenser tube to the target area. After the topical anesthetic is administered, the user can pull the dispenser plunger (together with the dispenser tube and needle cover) in the opposite direction to expose the needle tip. Pushing the syringe plunger can move the rubber stopper through the second carpule and thereby eject fluid from the carpule through the needle.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
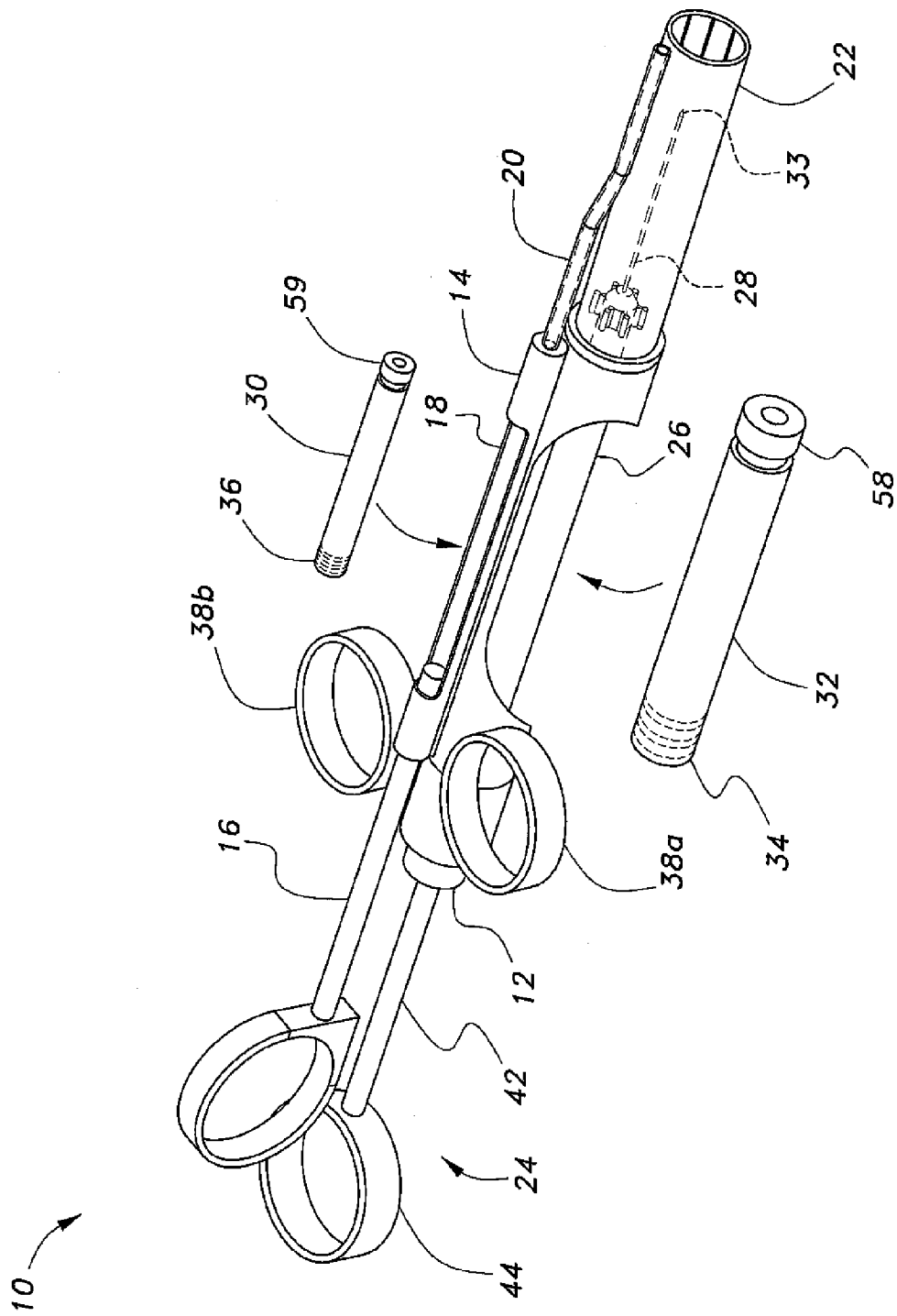
FIG. 1 is an environmental perspective view of a dental instrument according to the present invention, showing the first and second carpules outside of the dispenser barrel and the syringe barrel, respectively.

Referring to FIG. 1, the dental instrument 10 includes a syringe 12 and a topical anesthetic dispenser 14 that is slidably mounted on the syringe 12. The topical anesthetic dispenser 14 can include a dispenser plunger 16, a dispenser barrel 18 to which the dispenser plunger 16 is slidably attached, a dispenser tube 20, and a needle cover 22 affixed to the dispenser tube 20. The syringe 12 can include a syringe plunger 24, a syringe barrel 26 to which the syringe plunger 24 is slidably attached, and a hollow needle 28 having a beveled front end 33 defining an injection opening and an opposite rear end extending toward the syringe barrel 26. The syringe 24 can further include two grip handle rings 38a and 38b, respectively, through which a user's index finger and middle finger can be inserted to hold the dental instrument 10 in place. A first carpule 30 containing topical anesthetic can be loaded in the dispenser barrel 18. A second carpule 32 containing injectable anesthetic solution can be loaded in the syringe barrel 26. The first and second carpules 30 and 32, respectively, can include a generally cylindrical glass vial having openings at first and second opposing ends. The first end of each of the vials is covered by a rubber membrane that is held in place by a cap 58 and 59, respectively, made of metal foil. The metal cap 58, 59 of each vial has a circular opening at its center that exposes a portion of the rubber membrane. The rubber membrane of the first carpule 30 and the second carpule 32 can be pierced by a rear end of the dispenser tube 20 and the needle 28, respectively. The second end of each vial is closed by a movable rubber stopper 34 and 36, respectively.

The dental instrument 10 can be made from chrome-plated brass, stainless steel, or any suitable material known in the art.

Figure 2:
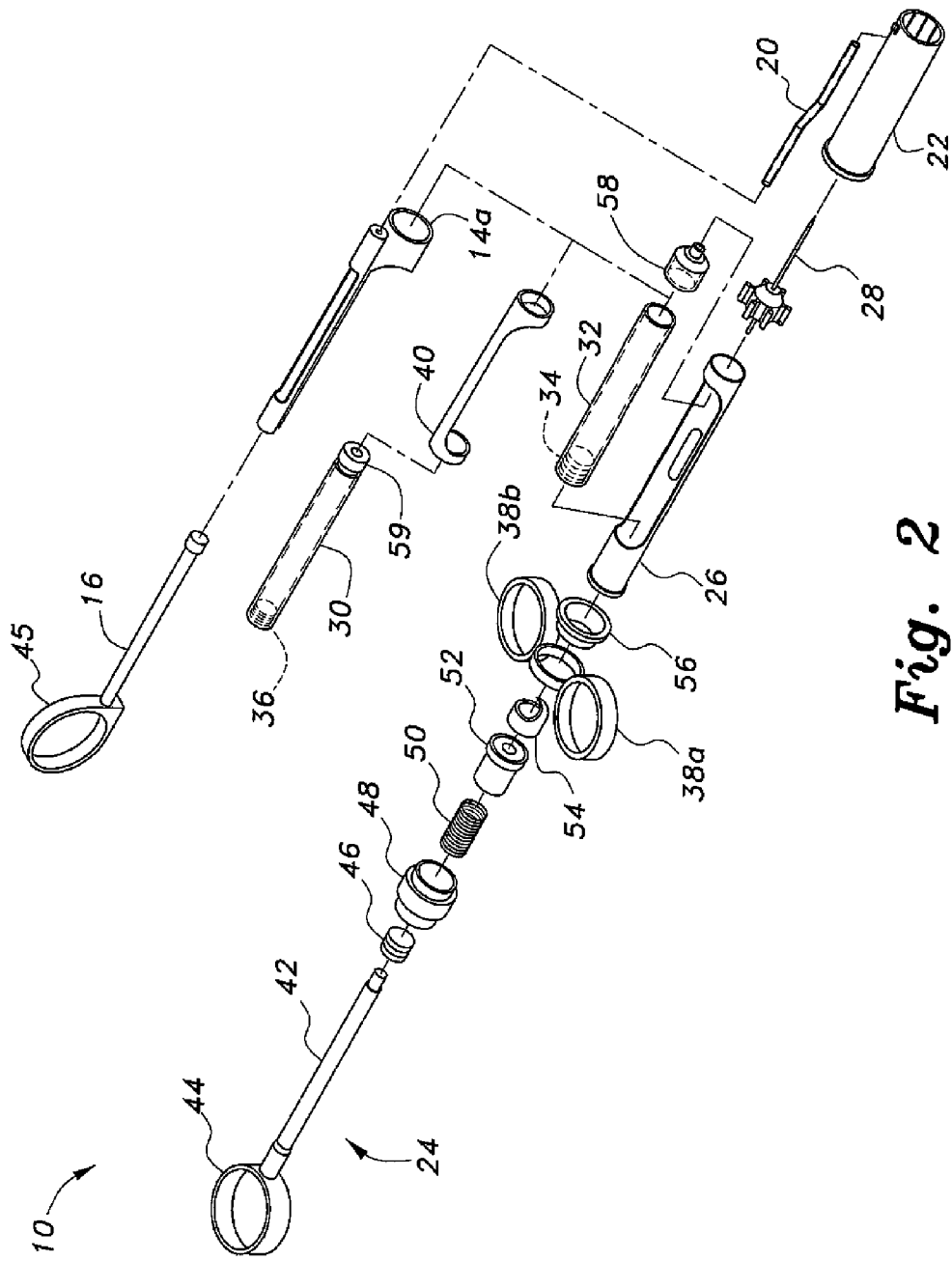
FIG. 2 is an exploded perspective view of the dental instrument of FIG. 1.

The syringe 12 and the dispenser 14 can be slidably connected in any suitable manner. As shown in FIG. 2, for example, an attachment bracket 40 can be provided which can be fitted within the syringe barrel 26, e.g., over the carpule 32, and slidably attached to the dispenser barrel 18. The attachment bracket 40 can include ring-like opposing ends for receiving opposing ends of the carpule 32. A bottom surface of the dispenser barrel 18 can, for example, include guide rails which slidably engage corresponding grooves defined in the attachment bracket. Alternatively, the dispenser barrel 18 can include grippers which slidably engage side edges of the attachment bracket. As is further shown, the dispenser barrel 16 can include a cylindrical protrusion 14a that receives an end portion of the syringe barrel 26. As such, the cylindrical protrusion 14a can have a diameter that is slightly larger than the end portion of the syringe barrel 26.

The syringe plunger 24 can include a shaft 42 having a ring handle 44 at one end and a piston 46 at an opposing end. A cylindrical housing member 48 can be positioned adjacent the piston 46. The cylindrical housing 48 can have a peripheral wall defining two opposing open ends. A compression spring 50 and a push knob 52 can be positioned within the cylindrical housing 48. A harpoon member 54 having a pointed or angled sharp edge can be at least partially disposed within the housing 48. The harpoon member 54 can be configured to engage a surface of the rubber stopper 34 of the carpule 32. For example, the harpoon 54 tip can be configured to hook into a top surface of the rubber stopper 34. A separating member 56 can be provided to separate the housing member from the syringe barrel 26.

The syringe plunger 24 can be configured to include an activating/locking mechanism that facilitates locking the compression spring 50 in a compressed state and/or releasing the compression spring 50. For example, the piston 46 can be rotationally constrained relative to the housing member 48. The piston 46 and the housing member 48 can, for example, include corresponding first and second threads, whereby twisting the syringe plunger 24 in a first direction compresses the compression spring 50, and twisting the syringe plunger 24 in an opposite second direction releases the compression spring 50. Upon release of the compression spring 50, the push knob 52 is pushed toward the carpule 32, which causes the harpoon 54 to latch into the rubber stopper 34 and the needle 28 to pierce the rubber membrane of the carpule cap 58. In other words, the push knob 52 can transmit load from the plunger 24 via the compression spring 50 to the rubber stopper 34.

Figure 3:
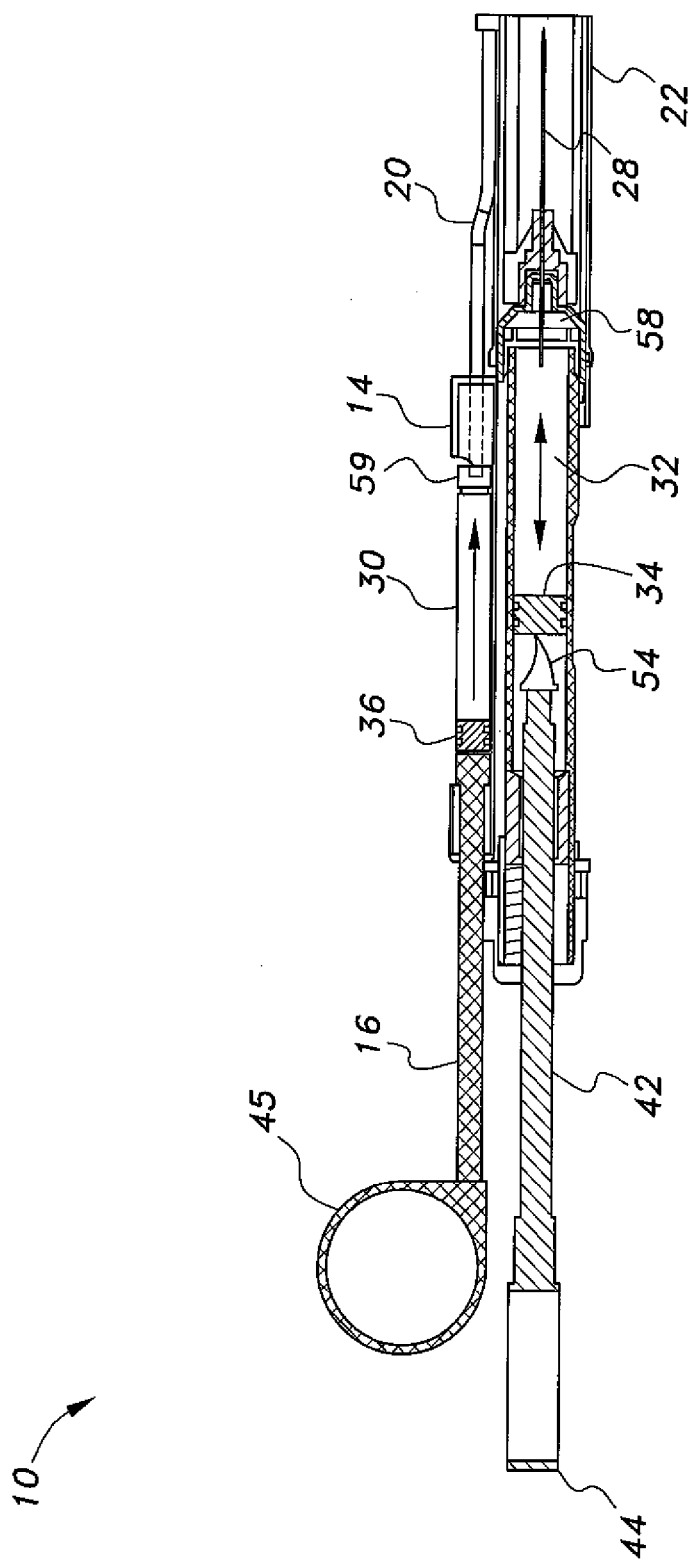
FIG. 3 is a side view in section of the dental instrument of FIG. 1.

As shown in FIG. 3, the first carpule 30 containing topical anesthetic can be loaded in the dispenser barrel 18 such that the rubber membrane of the cap 59 is penetrated by a rear end of the dispenser tube 20, and the rubber stopper 36 is in communication with the dispenser plunger 16. The front end of the dispenser tube 20 defines a dispenser opening or spray nozzle for dispensing topical anesthetic on the injection site. The second carpule 32 containing injectable anesthetic solution can be loaded in the syringe barrel 26 such that the cap 58 is proximate the rear end of the needle 28 and the rubber stopper 34 is proximate the harpoon 54 of the syringe plunger 24.

When not in use, the needle cover 22 can be positioned to extend circumferentially around the needle 28 and protrude beyond the needle tip 30, as shown in FIG. 1, to avoid accidental needle pricks. In use, a user can push the dispenser plunger 16 in the direction of a target area to thereby slide the dispenser barrel 18 forward and position the dispenser tube 20 (together with the attached needle cover 22) proximate a target area. Additional pressure on the dispenser plunger 16 can eject a spray of the topical anesthetic from the first carpule 30 through the dispenser tube 20 and to the target area. After the topical anesthetic is administered, the user can pull the dispenser plunger 16 (together with the dispenser tube 20 and needle cover 22) in the opposite direction to expose the needle tip 30. In other words, the dispenser tube 20 and needle cover 22 can slide in the direction of the user to expose the needle when the dispenser plunger 16 is pulled. The syringe plunger 24 can then be manipulated to release the compression spring 50. As described above, release of the compression spring 50 can advance the harpoon 54 forward to embed the harpoon tip 54 in the rubber stopper 34 and cause the rear end of the needle 28 to penetrate the rubber membrane of the cap 58. The needle tip 30 can then be inserted into a target area and the syringe plunger 24 can then be pushed forward to move the rubber stopper 34 through the second carpule 32 and eject fluid from the carpule 32 through the needle 28.

It should be noted that a user can, after inserting the needle tip 30 into a target area and prior to ejecting fluid from the carpule 32, withdraw a small amount of fluid from the target area by pulling the syringe plunger 24 in the direction of the user. Pulling the syringe plunger 24 can allow the harpoon 54 that is embedded in the rubber stopper 34 to elevate the rubber stopper 34 and thereby draw fluid into the carpule 32. Blood in the carpule 32 can indicate to a user that the needle 28 has penetrated a blood vessel and must be repositioned.

It is to be understood that the present invention is not limited to the embodiments described above, but encompasses any and all embodiments within the scope of the following claims.

We claim:

1. A dental instrument, comprising:
a topical anesthetic dispenser, including:
a cylindrical dispenser plunger including a first end having a first digit ring, and a second end opposite the first end;
a cylindrical dispenser barrel, the second end of the cylindrical dispenser plunger being slidably disposed in the cylindrical dispenser barrel, the cylindrical barrel being dimensioned and configured for receiving a first carpule containing topical anesthetic;
an elongate dispenser tube having a rear end adapted for penetrating the first carpule and a front end defining a spray nozzle, the cylindrical dispenser plunger being slidable in the cylindrical dispenser barrel to eject a spray of topical anesthetic from the first carpule onto an injection site to topically anesthetize injection site surface tissues prior to injection;
wherein the cylindrical dispenser plunger is selectively moved within the cylindrical dispenser barrel by manipulation of the first digit ring at the first end of the cylindrical dispenser plunger, causing the engagement of the first carpule to fluidly move the topical anesthetic from the carpule through the spray nozzle onto the injection site surface tissues; and
a needle cover affixed to the dispenser tube, the needle cover having an open end; and a cylindrical syringe, the cylindrical syringe including: a cylindrical syringe plunger having a syringe shaft, a first end including a second digit ring, and a second end opposite the first end;
a cylindrical syringe barrel, the second end of the cylindrical syringe plunger being slidably disposed in the cylindrical syringe barrel, the cylindrical syringe barrel being dimensioned and configured for receiving a second carpule containing an injectable anesthetic; and
an elongate hollow needle extending from the cylindrical syringe barrel, the needle having a rear end adapted for penetrating the second carpule and a pointed front end defining an injection opening, the cylindrical dispenser barrel being slidably mounted on the cylindrical syringe with the needle cover shrouded over the needle to prevent accidental needle sucks, the second end of the cylindrical syringe plunger being selectively slidable in the cylindrical syringe barrel by manipulation of the second digit ring moving the needle out of the open end of the needle cover into and beneath the injection site surface tissues that have been topically anesthetized, and injecting anesthetic from the second carpule thereunder.

2. The dental instrument according to claim 1, wherein the cylindrical syringe barrel further includes two grip handle rings, the grip handle rings being disposed on opposite sides of the cylindrical syringe barrel.

3. The dental instrument according to claim 1, further comprising a housing member having a peripheral wall, the housing member being in communication with the piston, the housing member including a compression spring within the peripheral wall of the housing member.

4. The dental instrument according to claim 3, wherein the piston is rotationally constrained within the housing member.

5. The dental instrument according to claim 3, further comprising a harpoon member having a sharp edge extending from the housing member, the sharp edge of the harpoon member being configured to penetrate a surface of a rubber stopper of the second carpule.

6. The dental instrument according to claim 5, further comprising a push knob disposed within the peripheral wall of the housing member, the push knob being disposed between the compression spring and the harpoon member.

7. The dental instrument according to claim 1, further comprising an attachment bracket disposed in the syringe barrel, the attachment bracket being slidably attached to a bottom surface of the dispenser barrel.

8. A combination syringe and anesthetic dispenser for locally anesthetizing tissue of a patient before an injection, the combination comprising: a syringe including:
- a syringe plunger consisting of a syringe shaft having a first end and a second end;
- a ring handle extending from the first end of the shaft; and a piston extending from the second of the shaft;
- a housing member having a cylindrical wall defining an outer periphery and an inner periphery, the housing having a first end and a second end having needle attached, and being dimensioned and configured for receiving a medicament carpule;
- wherein the piston is slidably disposed, and rotationally constrained within the inner periphery of the cylindrical wall of the housing member;
- wherein the shaft slidably extends through the first end of the housing;
- a compression spring disposed within the inner periphery of the cylindrical wall of the housing member;
- a harpoon member having a sharp edge extending therefrom;
- a push knob disposed within inner periphery of the cylindrical wall of the housing member, the push knob being disposed between the compression spring and the harpoon member;
- wherein the compression spring is adjacent to the piston, the push knob is adjacent to the compression spring, and the harpoon member is adjacent to the push knob; and
- wherein the compression spring, the piston, and the harpoon member are slidably movable within the inner periphery of the housing; and a pair of grip handle rings coupled to the housing;
- wherein the grip handle rings are disposed on opposite sides of the first end of the housing; and
- a topical anesthetic dispenser, consisting of:
- a dispenser barrel having a first end and a second end, the dispenser barrel being dimensioned and configured for receiving an anesthetic carpule; a dispenser plunger including a first end and a second end; wherein the first end of the dispenser plunger includes a digit ring; wherein the second end of the dispenser plunger is slidably disposed in the first end the dispenser barrel;
- an elongate dispenser tube having a rear end and a front end; the rear end being adjacent to the second end of the dispenser barrel, the elongate dispenser tube is adapted for penetrating any anesthetic carpule placed in the dispenser housing, and the front end defining a spray nozzle;
- wherein upon sliding the dispenser plunger into the dispenser barrel, any carpule disposed in the dispenser barrel is depressed, causing an ejection of topical anesthetic in a form of spray onto an injection site to locally anesthetize injection site tissues prior to a medicament injection; and
- a needle cover affixed to the dispenser tube, the needle cover having an open distal end, and a proximal end coupled to the second end of the housing of the syringe; and
- an attachment bracket operatively connected to the second end of the housing of the syringe, the attachment bracket being slidably attached to the dispenser barrel.

* * * * *